US011059777B2

(12) United States Patent
Male et al.

(10) Patent No.: US 11,059,777 B2
(45) Date of Patent: Jul. 13, 2021

(54) POLYMORPHIC FORMS OF BELINOSTAT AND PROCESSES FOR PREPARATION THEREOF

(71) Applicant: FRESENIUS KABI ONCOLOGY LTD., New Delhi (IN)

(72) Inventors: Sridhar Reddy Male, Gurgaon (IN); Saurabh Upadhyay, Gurgaon (IN); Suneel Kumar Sharma, Gurgaon (IN); Hrishikesh Acharya, Gurgaon (IN); Govind Singh, Gurgaon (IN); Saswata Lahiri, Gurgaon (IN); Walter Cabri, Milan (IT)

(73) Assignee: Fresenius Kabi Oncology Ltd., New Delhi (IN)

( * ) Notice: Subject to any disclaimer, the term of this patent is extended or adjusted under 35 U.S.C. 154(b) by 0 days.

(21) Appl. No.: 16/317,492

(22) PCT Filed: Jul. 25, 2017

(86) PCT No.: PCT/IB2017/054485
§ 371 (c)(1),
(2) Date: Jan. 11, 2019

(87) PCT Pub. No.: WO2018/020406
PCT Pub. Date: Feb. 1, 2018

(65) Prior Publication Data
US 2019/0241511 A1 Aug. 8, 2019

(30) Foreign Application Priority Data

Jul. 26, 2016 (IN) .......................... IN201611025483

(51) Int. Cl.
*C07C 311/37* (2006.01)
*C07C 311/21* (2006.01)
*C07C 303/40* (2006.01)
*A61P 35/00* (2006.01)
*C07C 303/44* (2006.01)

(52) U.S. Cl.
CPC ............ *C07C 311/21* (2013.01); *A61P 35/00* (2018.01); *C07C 303/40* (2013.01); *C07C 303/44* (2013.01); *C07C 311/37* (2013.01); *C07B 2200/13* (2013.01)

(58) Field of Classification Search
CPC ................................................... C07C 311/37
See application file for complete search history.

(56) References Cited

U.S. PATENT DOCUMENTS

2019/0256459 A1  8/2019  Pullagurla et al.

FOREIGN PATENT DOCUMENTS

| CN | 103787924 A | 5/2014 |
| CN | 104478769 B | 1/2016 |
| EP | 2 203 421 B1 | 5/2014 |
| JP | 2004-511462 A | 4/2004 |
| JP | 2009-508825 A | 3/2009 |
| JP | 2010-540426 A | 12/2010 |
| JP | 2011-500783 A | 1/2011 |
| WO | WO 02/30879 A2 | 4/2002 |
| WO | WO 2007/039403 A1 | 4/2007 |
| WO | WO 2009/040517 A2 | 4/2009 |
| WO | WO 2009/053808 A2 | 4/2009 |
| WO | WO 2017/199264 A1 | 11/2017 |

OTHER PUBLICATIONS

Polymorphism: in the Pharmaceutical Industry, 8 The Importance of Solvates, Ulrich J. Grieser, 2006, pp. 211-233.*
Cancer and Metastasis Reviews (1998), 17(1), 91-106.*
Science (1999), vol. 286, 531-537.*
Bao et al., "The Development of an Effective Synthetic Route of Belinostat," *Organic Process Research and Development* 20(8): 1482-1488 (2016).
Wang et al., Discovery of (2E)-3-{2-Butyl-1-[2-(diethylamino)ethyl]-1H-benzimidazol-5-yl}-N-hydroxyacrylamide (SB939), an Orally Active Histone Deacetylase Inhibitor with a Superior Preclinical Profile, *J. Med. Chem.* 54(13): 4694-4720 (2011).
European Patent Office, International Search Report in International Application No. PCT/IB2017/054485 (dated Oct. 17, 2017).
European Patent Office, Written Opinion in International Application No. PCT/IB2017/054485 (dated Oct. 17, 2017).
International Bureau of WIPO, International Preliminary Report on Patentability in International Application No. PCT/IB2017/054485 (dated Jan. 29, 2019).
Caira, "Crystalline Polymorphism of Organic Compounds" *Topics in Current Chemistry*, vol. 198, pp. 163-208, Springer, Berlin, Germany (1998).
Ashizawa, "Physico-Chemical Studies on the Molecular Details of Drug Crystals," *Pharm Tech Japan* 18(10): 81-96 (2002).
Mano, "Pharmaceutical research in the early stages of drug discovery—significance and practice," *Folia Pharmacologica Japonica* 133(3): 149-153 (2009).
Nakai et al., *New Pharmaceutics*, Shin-seiyakugaku, Nanzan-do, vol. 1 pp. 102-103 (Nov. 25, 1982).
*Polymorphism and crystallization of the pharmaceutical drugs*, Kazuhide Ashizawa, Editor/author, p. 273, 278, 305-317 (2002).
Stahly, Patrick., "The Importance of Salt Selection and Polymorph Screening for the Drug Product", *Journal of Pharmaceutical Science and Technology* 66(6): 435-439 (2006).

(Continued)

*Primary Examiner* — Rebecca L Anderson
(74) *Attorney, Agent, or Firm* — Leydig, Voit & Mayer, Ltd.

(57) ABSTRACT

The present invention relates to the polymorphic forms of Belinostat. The invention also relates to the process for the preparation of the polymorphic forms of Belinostat. This invention further relates to pharmaceutical composition of said polymorphic forms of Belinostat and use thereof in the treatment of a patient in need thereof.

9 Claims, 4 Drawing Sheets

(56) References Cited

OTHER PUBLICATIONS

Takata, "Cocrystal" *Pharm Tech Japan* 25(12): 155-166 (2009).
Yang et al., "Simple and Efficient Synthesis of Belinostat," Synthetic Communications 40(17): 2520-2524 (2010).
Japan Patent Office, Notice of Reasons for Refusal in Japanese Patent Application No. 2019-504086 (dated Jun. 19, 2020).

* cited by examiner

POLYMORPHIC FORMS OF BELINOSTAT AND PROCESSES FOR PREPARATION THEREOF

CROSS-REFERENCE TO RELATED APPLICATIONS

This patent application is the U.S. national phase of International Patent Application No. PCT/IB2017/054485, filed on Jul. 25, 2017, which claims the benefit of Indian Patent Application No. IN201611025483, filed Jul. 26, 2016.

FIELD OF INVENTION

The present invention relates to the polymorphic forms of Belinostat and processes for their preparation. The present invention further describes a pharmaceutical composition comprising polymorphic forms of Belinostat and their use in the manufacture of medicaments for the treatment of cancer in a patient.

BACKGROUND OF THE INVENTION

Belinostat, chemically known as (2E)-N-hydroxy-3-(3-phenylsulfamoylphenyl) acrylamide, is represented by the formula I.

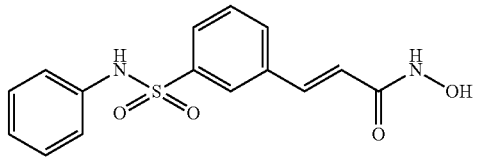

Formula I

Belinostat is the active ingredient of the drug Beleodaq® and is intended for intravenous administration. It is a histone deacetylase inhibitor indicated for the treatment of patients with relapsed or refractory peripheral T-cell lymphoma (PTCL).

Belinostat, as represented by the formula I, was described in WO 2002/030879. Example 7 of this PCT application describes the preparation of Belinostat, wherein a product was isolated after washing with acetonitrile and diethylether and has a melting point of 172° C.

An international patent application WO 2009/040517 describes a process for the synthesis of Belinostat, wherein a product is recrystallised from ethanol: water and is stated to yield a conglomerate of irregularly shaped birefringant crystals of Belinostat. However, this application does not provide any explicit information as to spectroscopic characterization data and does not specifically identify the polymorphic form of Belinostat.

A process for the synthesis of Belinostat is also described in Wang et al., *J. Med. Chem.* 2011, 54, 4694-4720, wherein Belinostat is purified by column chromatography using methanol and dichloromethane. The column chromatography is a time consuming process and thus not ideal for the commercial manufacturing of an API.

A particular polymorphic form of a compound may have physical properties that differ from those of any other crystalline or amorphous forms and such properties may influence markedly the chemical and pharmaceutical processing of the compound, particularly when the compound is prepared or used on a commercial scale. For example, each crystal form of a compound may show differences in physical properties such as crystalline size and shape, melting point, density, hygroscopicity and stability. Different crystalline forms of a compound may have different thermodynamic stabilities. In general, the more stable form, for example the more stable crystalline form, is generally the more suitable physical form for formulation and processing on a commercial scale.

Thus, there is a need for a solid form of Belinostat possessing desirable processing properties, such as ease of purification and storage stability. Also, there is a need for intermediate crystal forms that facilitate conversion to other polymorphic forms. New polymorphic forms and solvates of a pharmaceutically useful compound or salt thereof can also provide an opportunity to improve the performance characteristics of an API. It may give advantage by providing a product with the better quality of final API in terms of purity and yield.

It has now been found that under certain conditions solvated as well non-solvated polymorphic forms of Belinostat can be prepared. Thus, the present invention relates to new polymorphic forms of Belinostat that have advantageous properties. Such advantageous properties may for example be high chemical purity, a low content in residual solvents and long lasting storage stability etc. Similarly desirable is an advantageous morphology/crystal habit, stability against thermal and mechanical stress, and resistance to polymorphic conversion.

SUMMARY OF THE INVENTION

The present invention relates to the polymorphic forms of Belinostat and processes for preparing them. The present invention further relates to pharmaceutical compositions comprising such polymorphic forms of Belinostat and to the use thereof in the treatment of a patient in need thereof.

In a first aspect, the present invention relates to an acetone solvate of Belinostat.

In a second aspect, the present invention relates to a crystalline acetone solvate of Belinostat.

In a third aspect, the present invention relates to a process for the preparation of the acetone solvate of Belinostat, comprising the steps of:
a. contacting Belinostat with acetone; and
b. isolating the acetone solvate of Belinostat.

In a fourth aspect, the present invention relates to a crystalline form I of Belinostat, characterized by an X-ray powder diffraction (XRPD) pattern comprising peaks at about 14.7, 20.8, 21.2 and 26.4±0.2 degrees two-theta.

In a fifth aspect, the present invention relates to a process for the preparation of the crystalline form I of Belinostat, comprising the steps of:
a. dissolving the acetone solvate of Belinostat in a polar protic solvent;
b. adding a suitable anti-solvent to a solution of step a); and
c. isolating the crystalline form I of Belinostat.

In a sixth aspect, the present invention relates to the crystalline form I of Belinostat, wherein the crystalline form I of Belinostat is obtainable by the process comprising the steps of:
a. dissolving the acetone solvate of Belinostat in a polar protic solvent;
b. adding a suitable anti-solvent to a solution of step a); and
c. isolating the crystalline form I of Belinostat.

In a seventh aspect, the present invention relates to a process for the preparation of the crystalline form I of Belinostat, comprising the steps of:
a. contacting the acetone solvate of Belinostat with water; and
b. isolating the crystalline form I of Belinostat.

In a eighth aspect, the present invention relates to the crystalline form I of Belinostat, wherein the crystalline form I of Belinostat is obtainable by the process comprising the steps of:
a. contacting the acetone solvate of Belinostat with water; and
b. isolating the crystalline form I of Belinostat.

In a ninth aspect, the present invention relates to a pharmaceutical composition comprising acetone solvate of Belinostat or crystalline form I of Belinostat or mixture thereof and at least one pharmaceutically acceptable excipient.

In a tenth aspect, the present invention relates to a method of treating cancer, comprising administering a therapeutically effective amount of the acetone solvate of Belinostat or the crystalline form I of Belinostat or mixture thereof.

In an eleventh aspect, the present invention relates to a method of treating relapsed or refractory peripheral T-cell lymphoma (PTCL) or malignant thymoma, comprising administering a therapeutically effective amount of the acetone solvate of Belinostat or the crystalline form I of Belinostat or mixture thereof.

In a twelfth aspect, the present invention provides a method of preparing a pharmaceutical composition, comprising a step of admixing an acetone solvate of Belinostat or the crystalline form I of Belinostat or mixture thereof, with one or more pharmaceutically acceptable excipients.

Definitions

As used herein, the term 'ambient temperature_ refers to a temperature ranging from about 15° C. to 35° C., preferably the ambient temperature refers to a temperature from about 20° C. to 30° C., more preferably to a temperature of 25° C.

As used herein, the term 'anti-solvent_ refers to a liquid that, when combined with a solution of Belinostat reduces solubility of Belinostat in the solution, causing crystallization or precipitation in some instances spontaneously, and in other instances with additional steps such as seeding, cooling, scratching and/or concentrating.

As used herein, the term 'solvate_ refers to the crystalline solid adducts containing either stoichiometric or nonstoichiometric amounts of a solvent incorporated within the crystal structure.

As used herein, the term "contacting" includes mixing, adding, slurrying, stirring, or a combination thereof.

As used herein, the terms 'about_ are to be construed as modifying a term or value such that it is not an absolute. Such terms will be defined by the circumstances. This includes, at the very least, the degree of expected experimental error, technique error and instrument error for a given technique used to measure a value.

As used herein, the term 'alkyl_ means a straight chain, branched chain, or cyclic hydrocarbon radical, including but not limited to, methyl, ethyl, n-propyl, iso-propyl, n-butyl, sec-butyl, t-butyl, pentyl, n-hexyl, and cyclohexyl.

The term "substantially the same" with reference to analytical characterization such as X-ray powder diffraction (XRPD) peak positions or TGA thermogram endothermic/exothermic peak positions means that typical peak position and intensity variability are taken into account. For example, one skilled in the art will appreciate that the peak positions (2 theta) will show some inter-apparatus variability, typically as much as 0.2°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only.

ABBREVIATIONS

XRPD X-ray powder diffraction
TGA Thermal gravimetric analysis
$^{13}$C-NMR Carbon-13 nuclear magnetic resonance
IR Infrared spectroscopy
HPLC High Performance Liquid Chromatography

DETAILED DESCRIPTION OF THE INVENTION

A study on Belinostat has been performed to develop polymorphic forms which have advantageous properties. A wide range of re-crystallization solvents of various polarities were investigated. One solvate was identified as of interest, which is acetone solvate of Belinostat. From most of these solvents, a single non-solvated crystalline form of Belinostat was obtained which is hereinafter referred as 'crystalline form I of Belinostat_.

The polymorphic forms of Belinostat according to the present invention may be characterized using various techniques. Examples of characterization methods include, but are not limited to, single crystal X-ray diffraction, X-ray powder diffraction (XRPD), simulated powder X-ray patterns, solid state $^{13}$C-NMR, Raman spectroscopy, infrared spectroscopy (IR), moisture sorption isotherms, thermal gravimetric analysis (TGA), differential scanning calorimetry (DSC) and hot stage techniques.

The acetone solvate and the crystalline form I of Belinostat are characterized by X-ray powder diffraction (XRPD) and thermal gravimetric analysis (TGA).

In a first aspect, the present invention relates to an acetone solvate of Belinostat. The present invention relates to an acetone solvate of Belinostat, wherein the molar ratio of Belinostat to acetone solvent is about 1:0.75-0.95. The acetone solvate of Belinostat contains about 8.5±1% by weight of acetone.

Further, inventors have found that acetone solvate of Belinostat, possess a crystalline physical form, which is easily isolated and is also very stable. Moreover, this solvate may readily be prepared on a commercial scale with high purity and high yield.

In a second aspect, the present invention relates to a crystalline acetone solvate of Belinostat.

Figure 1:
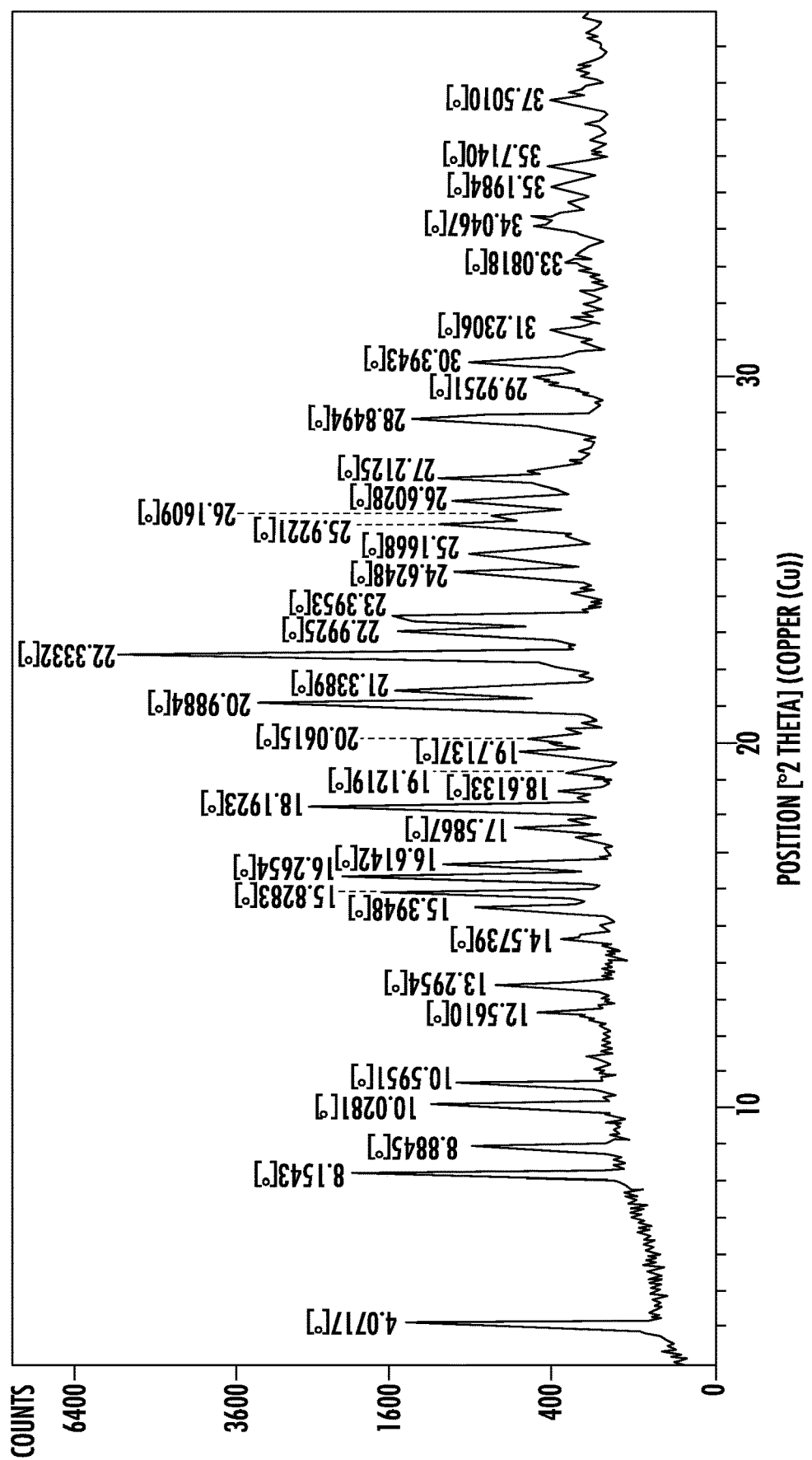
FIG. 1; represents an X-ray powder diffraction (XRPD) pattern of the crystalline acetone solvate of Belinostat of the present invention FIG. 2; represents a thermal gravimetric (TGA) analysis of the crystalline acetone solvate of Belinostat of the present invention FIG. 3; represents an X-ray powder diffraction (XRPD) pattern of the crystalline form I of Belinostat of the present invention FIG. 4; represents a thermal gravimetric analysis (TGA) of the crystalline form I of Belinostat of the present invention
Figure 2:
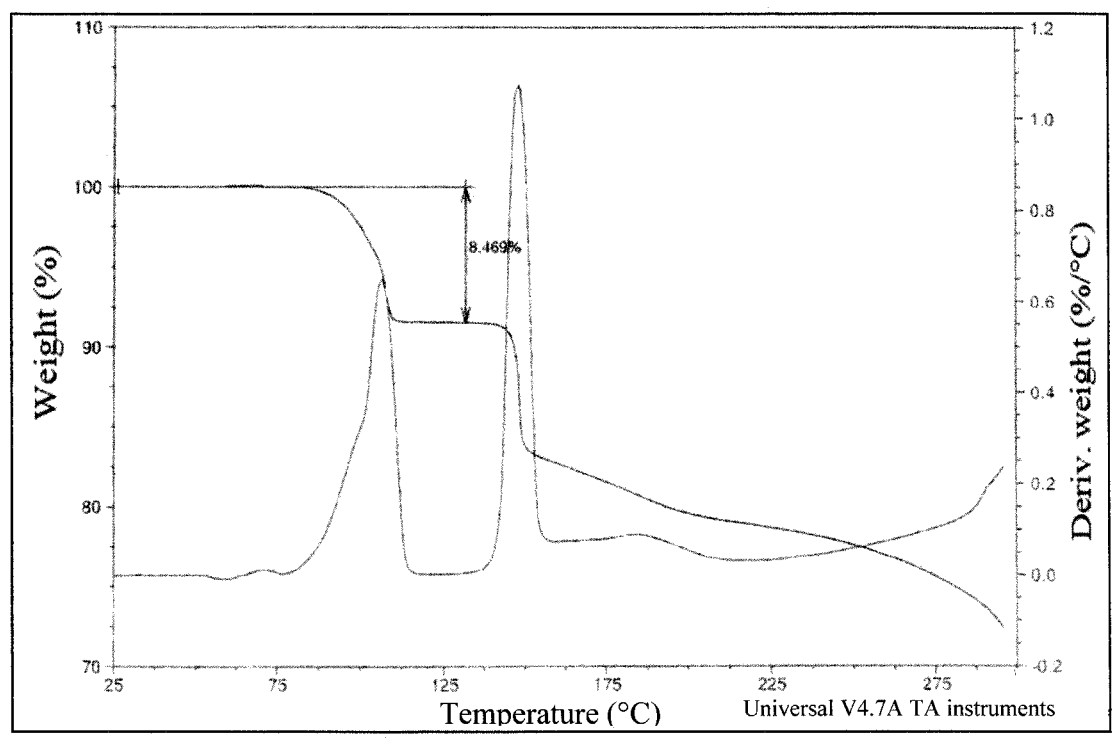

The crystalline acetone solvate of Belinostat is characterized by at least one of the following:
a. an X-ray powder diffraction (XRPD) pattern comprising peaks at about 16.3, 18.2, 21.0 and 22.3±0.2 degrees two-theta;
b. an X-ray powder diffraction (XRPD) pattern substantially the same as depicted in FIG. 1;
c. by a weight loss of about 8.5±1% as measured by thermal gravimetric analysis (TGA); and
d. a thermal gravimetric thermogram substantially the same as depicted in FIG. 2.

The crystalline acetone solvate of Belinostat can be further characterized by an X-ray powder diffraction (XRPD) pattern comprising peaks at about 4.1, 8.2, 15.8, and 21.3±0.2 degrees two-theta.

Belinostat used as a starting material in the present invention may be prepared according to the methods known in art such as described in WO 2002/030879, WO 2009/040517, J. Med. Chem. 2011, 54, 4694-4720 or as described herein. Belinostat, starting material of the present invention, may be prepared by reacting the compound of formula II,

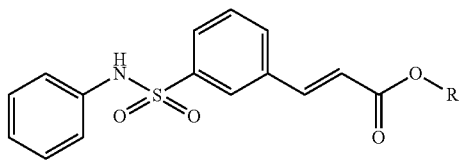

Formula II wherein R is alkyl
with hydroxylamine hydrochloride in the presence of a base to give Belinostat.

The base used in the reaction may be selected from the group consisting of alkali metal hydroxide and alkali metal alkoxide, preferably base may be selected from sodium hydroxide, potassium hydroxide, sodium alkoxide or potassium alkoxide; more preferably sodium methoxide or sodium tert-butoxide. The reaction may be carried out in a suitable solvent. A suitable solvent is alcohol, preferably methanol or ethanol. The reaction of the compound of formula II with hydroxylamine hydrochloride in the presence of a base may be carried out at a temperature of 0-60° C., preferably at 0° C. to ambient temperature followed by stirring for a period of 30 minutes to 10 hours. Preferably, the reaction is completed in 1 to 4 hours to give Belinostat. Belinostat may be isolated from the reaction mixture by the methods such as extraction, precipitation, cooling, filtration, centrifugation or combination thereof; preferably Belinostat is isolated by filtration or extraction.

In a third aspect, the present invention relates to a process for the preparation of the acetone solvate of Belinostat, comprising the steps of:
a. contacting Belinostat with acetone; and
b. isolating the acetone solvate of Belinostat.

Step a) may be carried out at 10-70° C. for 10 minutes to 12 hours to convert Belinostat to its acetone solvate, preferably reaction is carried out at 15 to 60° C. for 20 minutes to 4 hours.

The acetone solvate of Belinostat may be isolated by methods such as precipitation, cooling, filtration, centrifugation or combination thereof. The acetone solvate may be isolated by cooling the resulting reaction mixture to 0-10° C. followed by filtration.

The acetone solvate of Belinostat may optionally be washed with acetone.

Thus obtained acetone solvate of Belinostat is optionally dried by the methods such as vacuum drying, heat drying, spray drying, freeze drying, supercritical drying or natural air drying. Any of the mentioned methods may also be used in combination to ensure removal of unbound solvent. Preferably the acetone solvate of Belinostat is dried by vacuum drying method. As will be recognized, the drying time will be dependent upon, amongst other things, the amount of material to be dried, and the particular drying method used. Generally a drying time of 20 minutes to 20 hours, preferably 1 to 12 hours is sufficient. Conveniently the drying is performed under vacuum and optionally under inert atmosphere, for example by passing a stream of warm inert gas such as nitrogen over or through the material.

The process described above may be varied, for example in terms of the quantity of the starting Belinostat that is treated, the volume of the acetone, the temperature of the treatment, cooling phases and/or drying conditions.

In a fourth aspect, the present invention relates to a crystalline form I of Belinostat.

Figure 3:
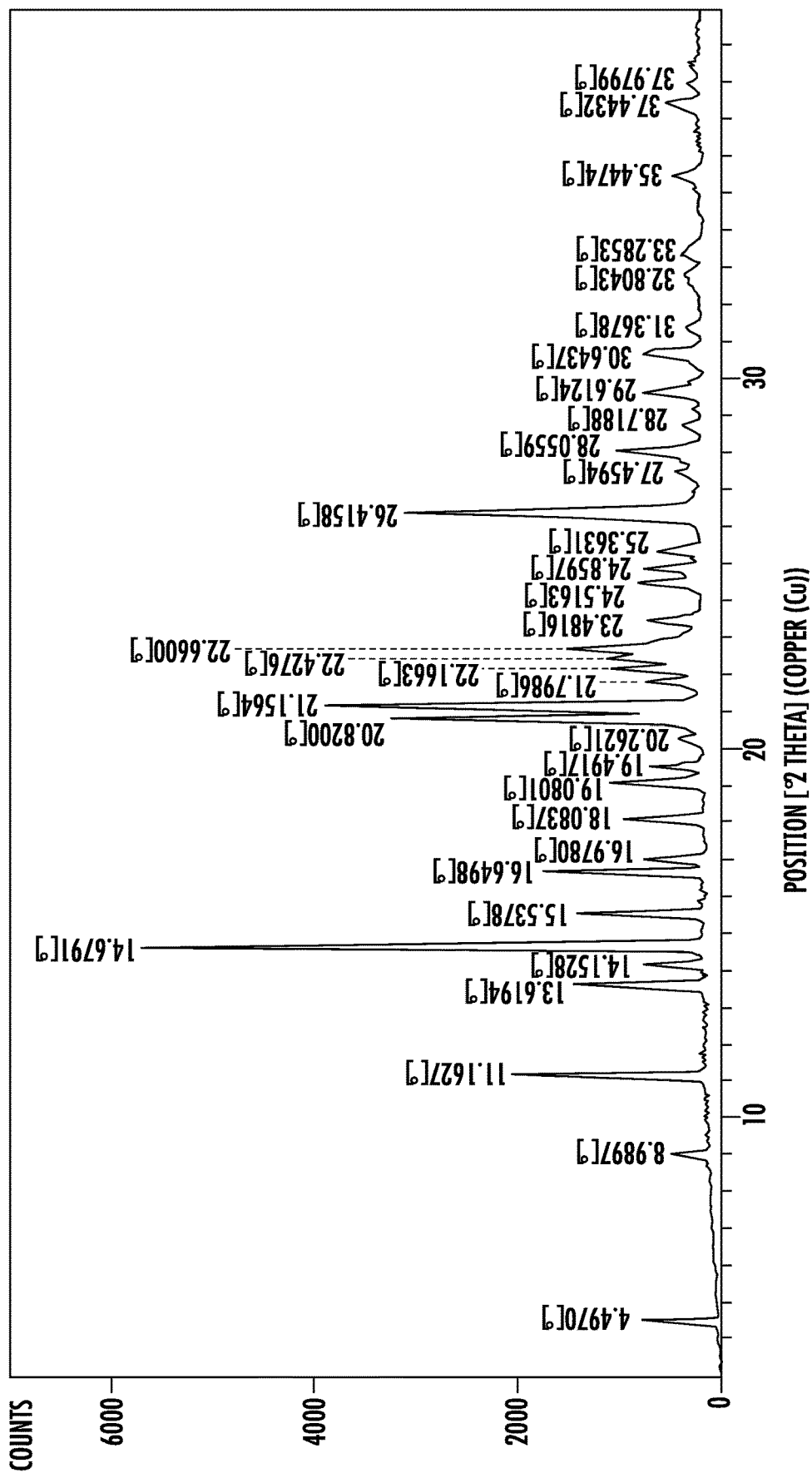
Figure 4:
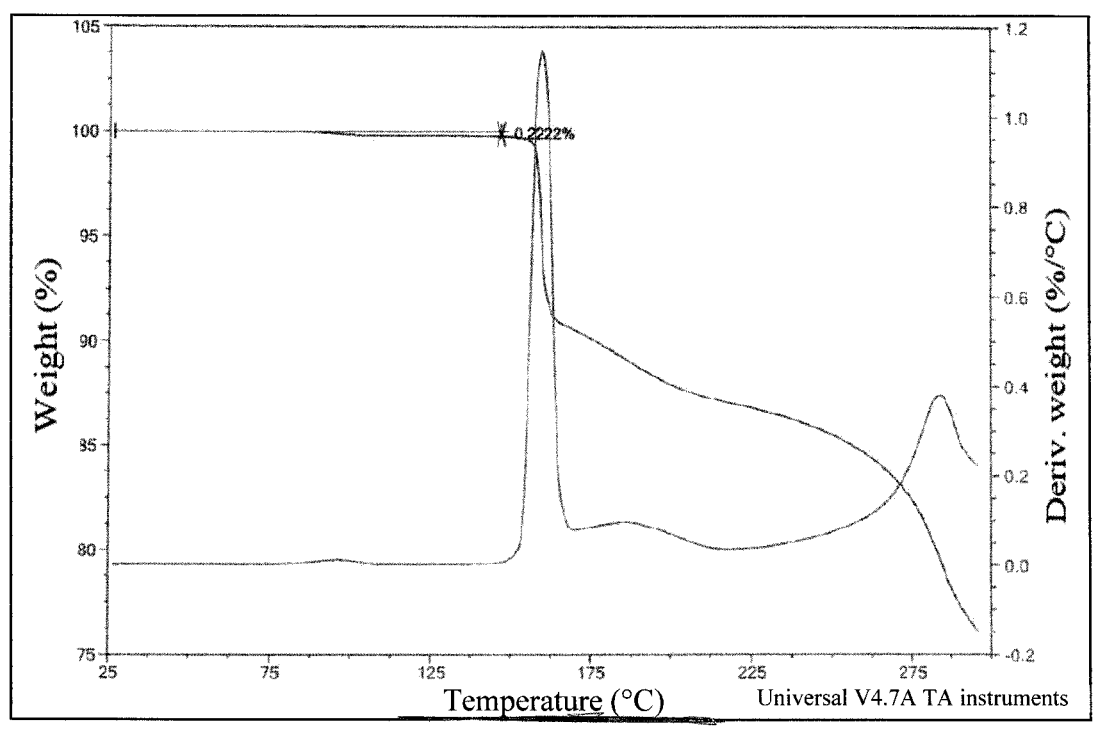

The crystalline form I of Belinostat is characterized by at least one of the following:
a. an X-ray powder diffraction (XRPD) pattern comprising peaks at about, 14.7, 20.8, 21.2 and 26.4±0.2 degrees two-theta;
b. an X-ray powder diffraction (XRPD) pattern substantially the same as depicted in FIG. 3;
c. by a weight loss of about less than 1% as measured by thermal gravimetric analysis (TGA); and
d. a thermal gravimetric thermogram substantially the same as depicted in FIG. 4.

The crystalline form I of Belinostat can be characterized by an X-ray powder diffraction (XRPD) pattern further comprising peaks at about 11.2, 13.7, and 16.7±0.2 degrees two-theta.

In a fifth aspect, the present invention relates to the process for the preparation of the crystalline form I of Belinostat, comprising the steps of:
a. dissolving the acetone solvate of Belinostat in a polar protic solvent;
b. adding a suitable anti-solvent to a solution of step a); and
c. isolating the crystalline form I of Belinostat.

The polar protic solvent used in step a) is selected from $C_{1-4}$ alcohols, preferably methanol or ethanol.

The mixture of the acetone solvate of Belinostat and polar protic solvent may be stirred at ambient temperature or be heated to reflux until dissolution has occurred. Alternatively, the mixture may, for example, be heated to a temperature less than the reflux temperature of the solvent provided that dissolution of more or less all of the solid material has occurred. It will be appreciated that small quantities of insoluble material may be removed by filtration of the mixture.

The solution obtained after step a) may optionally be treated with activated carbon at elevated temperature; preferably 35-55° C. followed by cooling to ambient temperature. The activated carbon may be removed by method such as filtration through hyflow.

The resulting solution after step a), with or without activated carbon treatment, is mixed with a suitable anti-solvent to precipitate the product from the solution. The suitable anti-solvent is water. The mixture can be stirred for a period of 30 minutes to 12 hours, preferably for 1 to 3 hours, at a suitable temperature, preferably ambient temperature for the preparation of crystalline form I of Belinostat.

The crystalline form I of Belinostat may be isolated from the resulting mixture by the methods such as precipitation, cooling, filtration, centrifugation or combination thereof. Preferably the crystalline form I of Belinostat is isolated by vacuum filtration.

The crystalline form I of Belinostat may optionally be washed with a suitable anti-solvent.

The material obtained is optionally dried by the methods such as vacuum drying, heat drying, spray drying, freeze drying, supercritical drying or natural air drying. Any of the mentioned methods may also be used in combination to ensure complete removal of solvent and anti-solvent. Preferably, the crystalline form I of Belinostat is dried by heat and/or vacuum drying methods. A suitable drying temperature is, for example, from 35 to 100° C., particularly from 45 to 65° C. As will be recognized, the drying time will be dependent upon, amongst other things, the amount of material to be dried, and the particular drying method used. Generally a drying time of 20 minutes to 25 hours, preferably 5 to 22 hours is sufficient. Conveniently the drying is performed by heating under vacuum and optionally under inert atmosphere, for example by passing a stream of warm inert gas such as nitrogen over or through the material.

The process described above may be varied, for example in terms of the quantity of the acetone solvate of Belinostat that is treated, the volume of the solvent or anti-solvent, the temperature of the treatment, cooling phases and/or drying conditions.

In a sixth aspect, the present invention relates to the crystalline form I of Belinostat, wherein the crystalline form I of Belinostat is obtainable by the method as described above.

In a seventh aspect, the present invention relates to the process for the preparation of the crystalline form I of Belinostat, comprising the steps of:
a. contacting the acetone solvate of Belinostat with water; and
b. isolating the crystalline form I of Belinostat.

Step a) may be carried out at ambient temperature, preferably at 20-30° C. and for 30 minutes to 12 hours to convert the acetone solvate to crystalline form I of Belinostat, preferably for 1-3 hours.

The crystalline form I of Belinostat may be isolated by the methods such as precipitation, cooling, filtration, centrifugation or combination thereof; preferably crystalline form I of Belinostat is isolated by vacuum filtration.

The crystalline form I of Belinostat may optionally be washed with water.

The material obtained is optionally dried by the methods such as vacuum drying, heat drying, spray drying, freeze drying, supercritical drying or natural air drying. Any of the mentioned methods may also be used in combination to ensure complete removal of water and conversion to the desired crystalline form I of Belinostat. Preferably the crystalline form I of Belinostat is dried by heat and/or vacuum drying methods. A suitable drying temperature is, for example, from 35 to 100° C., particularly from 45 to 65° C. As will be recognized, the drying time will be dependent upon, amongst other things, the amount of material to be dried, and the particular drying method used. Generally a drying time of 30 minutes to 25 hours, for example 5 to 20 hours is sufficient. Conveniently the drying is performed by heating under vacuum and optionally under inert atmosphere, for example by passing a stream of warm inert gas such as nitrogen over or through the material.

The process described above may be varied, for example in terms of the quantity of the acetone solvate of Belinostat that is treated, the volume of the water, the temperature of the treatment, cooling phases and/or drying conditions.

In an eighth aspect, the present invention relates to the crystalline form I of Belinostat, wherein the crystalline form I of Belinostat is obtainable by the method as described above.

It has been found that the acetone solvate of Belinostat may readily be converted into the crystalline form I of Belinostat by the process of the present invention. Overall, the inclusion of the steps of acetone solvate preparation and conversion back to the crystalline form I of Belinostat is beneficial in terms of yield and purity of the final active pharmaceutical ingredient (API), Belinostat. The preparation of acetone solvate of Belinostat and further conversion to unsolvated Belinostat, preferably crystalline form I of Belinostat, may be repeated to enhance the purity of final product or to reduce the impurity level in the final product.

In a ninth aspect, the present invention relates to a pharmaceutical composition comprising the acetone solvate of Belinostat or crystalline form I of Belinostat or mixture thereof and at least one pharmaceutically acceptable excipient.

In a tenth aspect, the present invention relates to a method of treating cancer, comprising administering a therapeutically effective amount of the acetone solvate of Belinostat or the crystalline form I of Belinostat or mixture thereof.

In an eleventh aspect, the present invention relates to a method of treating relapsed or refractory peripheral T-cell lymphoma (PTCL) or malignant thymoma, comprising administering a therapeutically effective amount of the acetone solvate of Belinostat or the crystalline form I of Belinostat or mixture thereof.

In a twelfth aspect, the present invention provides a method of preparing a pharmaceutical composition, comprising a step of admixing an acetone solvate of Belinostat or the crystalline form I of Belinostat or mixture thereof, with one or more pharmaceutically acceptable excipients.

The methods for the preparing polymorphic forms of Belinostat of the present invention may be illustrated by way of the following examples, which in no way should be construed as limiting the scope of the invention.

EXAMPLES

Instruments

XRPD

X-ray diffraction data is obtained using a Bruker AXS D8 advance powder X-ray Diffractometer, CuK radiation, wavelength 1.54 Å.

TGA

TGA measurement is performed using a TGA Q500 V20, temperature range 25-300° C. and 10° C./min.

Reference Example 1: Preparation of Sodium 3-formylbenzenesulfonate

Benzaldehyde (10.0 g) was slowly added into the oleum solution (25.0 mL), not exceeding temperature above 30°, and reaction mass was stirred for 10 hours at 40-45° C. and then at ambient temperature for 5-6 hours. The reaction mass was poured into ice/water and extracted with ethyl acetate (50 mL). Thereafter, pH of the aqueous layer was adjusted to 6-7 with CaCO$_3$ and reaction mixture was filtered. pH of the filtrate was adjusted to 8-9 with sodium carbonate, again filtered and concentrated the filtrate under vacuum to obtain 6.8 g of sodium 3-formylbenzenesulfonate.

Reference Example 2: Preparation of 3-formylbenzene-1-sulfonic acid

Benzaldehyde (100 g) was added into the 20% oleum solution (500 mL) and reaction mass was stirred for 12-15 hours at 70-80° C. Thereafter, reaction mass was cooled to 0-10° C. and poured into ice/water. Sodium hydroxide (500 mL) and methanol (1500 mL) was added to the reaction mass followed by stirring for 1 hour at 10-20° C. The pH of reaction mixture was adjusted to 2.0 to 3.0 by addition of dilute sulfuric acid (100 mL). The reaction mixture was stirred for 10-15 minutes at 10-20° C., filtered, washed with methanol (2×500 mL) and filtrate was evaporated under vacuum. Toluene (500 mL) was added to resulting residue, stirred for 10-20 minutes at 50-60° C. and solvent was evaporated under vacuum. Thereafter, methanol (1500 mL) was added to the resulting residue, stirred, treated with activated carbon and solvent was evaporated. Dimethylformamide (800 mL) was added to reaction mass, stirred for 50-70 minutes at 40-50° C. and filtered thorugh hyflo bed. Solvent was partially recovered from the reaction mixture followed by addition of ethyl acetate (1500 mL). The reaction mixture was stirred for 1-2 hours at 20-30° C., filtered, washed with ethyl acetate and dried under vacuum to obtain 155 g of 3-formylbenzene-1-sulfonic acid.

Reference Example 3: Preparation of Sodium 3-[(1E)-3-methoxy-3-oxoprop-1-en-1-yl]benzenesulfonate Method A:
Sodium 3-formylbenzenesulfonate (7.0 g), potassium carbonate (9.2 g), trimethyl phosphonoacetate (6.5 mL) and water (17.5 mL) were stirred for 2 hours at 20-25° C. Solid was filtered. The filtrate was concentrated under vacuum to obtain 6.5 g of sodium 3-[(1E)-3-methoxy-3-oxoprop-1-en-1-yl]benzenesulfonate.

Method B:
Sodium-3-formylbenzenesulfonate (30.0 g) was added in methanol (120 mL) at room temperature and the reaction mass was cooled to 0-10° C. Trimethylphophonoacetate (26.2 g) and sodium methoxide solution (37.3 mL) was added to reaction mass at 0-10° C. and stirred for 2 hours. After completion of the reaction, reaction mass was allowed to reach room temperature and then acetone (60 mL) was added. The reaction mass was stirred for 30-40 minutes and filtered the solid. Thus obtained solid was dried under vacuum at 45-50° C. to give 26 g of sodium 3-[(1E)-3-methoxy-3-oxoprop-1-en-1-yl]benzenesulfonate.

Method C:
3-Formylbenzene-1-sulfonic acid (150 g) in dimethylformamide (750 mL) was stirred for 10-20 minutes at 20-30° C. followed by addition of trimethylphosphonoacetate (152.5 g) and sodium methoxide solution (prepared by dissolving 45.2 g of sodium methoxide in 225 mL of methanol). The reaction mixture was stirred for 1-2 hours at 0-10° C. followed by addition of diisopropyl ether (3000 mL). The reaction mixture was stirred for 1-2 hours at 20-30° C., filtered, washed with diisopropyl ether (2×300 mL) and dried under nitrogen atmosphere. Methanol (3750 mL) was added to the resulting product, stirred for 20-30 minutes at 35-40° C., filtered through hyflo bed and washed with methanol. Solvent was partially recovered from the reaction mixture under vacuum and ethyl acetate (2250 mL) was added to resulting mass at 50-60° C. The mixture was cooled to 20-30° C., stirred for 2-3 hours, filtered, washed with ethyl acetate and dried under vacuum to give 104 g of sodium 3-[(1E)-3-methoxy-3-oxoprop-1-en-1-yl]benzenesulfonate.

Reference Example 4: Preparation of methyl (2E)-3-[3-(phenylsulfamoyl) phenyl]prop-2-enoate Method A:
Sodium 3-[(1E)-3-methoxy-3-oxoprop-1-en-1-yl]benzenesulfonate (5.0 g) was added in a solution of toluene (25 mL) and thionyl chloride (8.7 mL) under N2 atmosphere. Catalytic amount of DMF (0.3 mL) was added to reaction mass and refluxed for 2 hours. Reaction mass was filtered and the filtrate was distilled. The resulting residue was dissolved in dichloromethane (25 mL) (SOLUTION-1). To a mixture of aniline (4.3 mL) and triethylamine (7.5 mL), the dichloromethane solution (25 mL) (SOLUTION-1) was added and the mixture was stirred for 2-3 hours at 50° C. The reaction mass was distilled out and residual mass was added to ethyl acetate (25 mL) and water (25 mL). The organic layer was separated, washed with 10% HCl and brine solution. Solvent was removed by distillation from the resulting organic layer to obtain 1.0 g of methyl (2E)-3-[3-(phenylsulfamoyl) phenyl]prop-2-enoate.

Method B:
To a mixture of sodium 3-[(1E)-3-methoxy-3-oxoprop-1-en-1-yl]benzenesulfonate (100 g) in toluene (500 mL), dimethylformamide (10 mL) and thionyl chloride (90 g) was added and mixture was stirred for 2 to 2.5 hours at 55-65° C. The reaction mixture was distilled under vacuum. Toluene (600 mL) was added to the resulting residue, mixture was stirred for 10-20 minutes at 20-30° C., filtered and washed with toluene (200 mL). The organic layer was combined and cooled to 0-10° C. Aniline (42.3 g) and diisopropyl ethyl amine (58.7 g) was added to resulting organic layer and stirred for 2-2.5 hours at 20-30° C. Ethyl acetate (1500 mL) and water (500 mL) was added to the reaction mixture and stirred for 15-30 minutes. The organic layer was separated, washed with dilute HCl and 5% sodium bicarbonate solution. The organic layer was treated with activated carbon and solvent was removed by distillation from the resulting organic layer. The resulting residue was added to toluene (300 mL), stirred at 20-30° C., filtered and dried. Thereafter, methanol (2000 mL) was added to the resulting product, stirred at 55-60° C. for 15-30 minutes and solvent was recovered partially. The reaction mixture was cooled to ambient temperature, stirred for 1-1.5 hours, filtered, washed with methanol and dried under vacuum to obtain 92 g of methyl (2E)-3-[3-(phenylsulfamoyl) phenyl]prop-2-enoate.

Reference Example 5: Preparation of Belinostat

Method A:
To the mixture of methyl (2E)-3-[3-(phenylsulfamoyl) phenyl]prop-2-enoate (40 g) and hydroxylamine hydrochloride (52.55 g) in anhydrous methanol (400 mL), sodium methoxide in methanol solution (244.8 g, 25% w/w) was added under N$_2$ atmosphere and the reaction mass was stirred for 2-3 hours at 20-30° C. The salt was filtered and the filtrate was concentrated under reduced pressure. DM water was added to the resulting residue and pH was adjusted to 6-8 using dilute hydrochloric acid solution. The resulting mixture was extracted by ethyl acetate (2*520 mL) and layers were separated. The organic layer was washed with 7% sodium bicarbonate solution (2*400 mL) and DM water (400 mL). The resulting organic layer was concentrated under reduced pressure to obtain 36 g of Belinostat having purity of 97.59% by HPLC.

Method B:

To a mixture of methyl (2E)-3-[3-(phenylsulfamoyl) phenyl]prop-2-enoate (20.0 g), hydroxylamine hydrochloride (26.3 g) and methanol (100 mL), sodium tert-butoxide solution (54.5 g dissolved in 200 mL of methanol) was added slowly and stirred for 2 hours at ambient temperature. Reaction mass was filtered and mother liquor was distilled under vacuum. The residue was mixed with methanol (100 mL), water (260 mL) and ethyl acetate (260 mL) and then neutralized with concentrated hydrochloric acid (18 mL). The layers were separated. The organic layer was washed with sodium bicarbonate solution (2×200 mL), water (200 mL) and then with brine solution (200 mL). Resulting organic layer was concentrated under reduced pressure to obtain 18 g of Belinostat having purity of 99.08% by HPLC.

Method C:

To a mixture of methyl (2E)-3-[3-(phenylsulfamoyl) phenyl]prop-2-enoate (100 g), hydroxylamine hydrochloride (131.34 g) and methanol (200 mL), sodium methoxide solution (170.16 g dissolved in 856 mL of methanol) was added and stirred for 2-2.5 hours at 0-10° C. The residue was mixed with water (1200 mL) and ethyl acetate (1800 mL) and then pH was adjusted to 5-5.8 with dilute hydrochloric acid (18 mL). The layers were separated and aqueous layer was washed with ethyl acetate. The organic layer was combined, washed with brine solution (1000 mL) and sodium bicarbonate solution (1000 mL). Solvent was distilled from the resulting organic layer followed by addition of methanol (500 mL) and again distillation to obtain 100 g of Belinostat

Example 1: Preparation of Acetone Solvate of Belinostat

A mixture of Belinostat (100 g) in acetone (800 mL) was stirred for 20-30 minutes at 50-55° C. The mixture was cooled to 0-5° C., filtered, washed with acetone (100 mL) and suck dried for 30 minutes. Methanol (500 mL) was added to the resulting residue, stirred for 15-20 minutes at 20-30° C. and solvent was distilled off. Thereafter, resulting residue was mixed with acetone (600 mL) and stirred for 20-30 minutes at 50-55° C. The mixture was cooled to 0-5° C., stirred for 2-3 hours, filtered, washed with acetone (50 mL) and suck dried for 30 minutes to give 70 g of acetone solvate of Belinostat.

Example 2: Preparation of the Crystalline Acetone Solvate of Belinostat

A mixture of Belinostat (36 g) in acetone (480 mL) was stirred for 1-2 hours at 20-30° C. The solid was filtered, washed with acetone (40 mL) and suck dried for 30 minutes. The resulting product was finally dried under vacuum at 40° C. for 10 hours. 20 g of the crystalline acetone solvate of Belinostat was obtained in 99.96% purity by HPLC.

XRPD peaks: 4.072, 8.154, 15.828, 16.265, 18.192, 20.988, 21.339, 22.333, 22.992, 23.395 and 28.849±0.2 degrees two-theta Acetone content: 8.5% w/w

Example 3: Preparation of the Crystalline Form I of Belinostat

A mixture of the acetone solvate of Belinostat (13 g) and methanol (65 mL) was stirred for 10 minutes at 20-30° C. to obtain a clear solution. The resulting solution was treated with activated carbon (1.3 g), stirred for 30 minutes at 40-45° C., cooled to 20-30° C. and filtered through hyflow bed. The hyflow bed was washed with methanol (65 mL) and the filtrate was further filtered through micron filter. The resulting filtrate was added to DM water (520 mL), maintaining the temperature at 20-30° C. and stirred for 2 hours. The resulting mixture was filtered, washed with DM water (26 mL) and dried under vacuum at 50-55° C. for 20 hours. 10.5 g of the crystalline form I of Belinostat was obtained in 99.94% purity by HPLC.

XRPD peaks: 4.533, 9.049, 11.196, 13.575, 13.681, 14.722, 15.560, 16.686, 17.028, 18.127, 20.852, 21.204, 22.701, 26.459, 26.544, 28.087 and 30.696±0.2 degrees two-theta.

Wt. loss by TGA: 0.034% w/w

Example 4: Preparation of the Crystalline Form I of Belinostat

Mixture of the acetone solvate of Belinostat (2 g) and DM water (40 mL) was stirred for 1 hour at 20-30° C. The solid was filtered and washed with DM water (4 mL) followed by drying at 50-55° C. for 18 hours. 1.68 g of the crystalline form I of Belinostat was obtained in 99.97% purity by HPLC.

XRPD peaks: 4.497, 8.992, 11.162, 13.619, 14.151, 14.679, 15.536, 16.650, 16.979, 18.088, 19.079, 20.816, 21.158, 21.799, 22.164, 22.638, 24.518, 24.862, 26.416, 26.499, 28.055, 29.622 and 30.688±0.2 degrees two-theta.

Wt. loss by TGA: 0.22% w/w

Example 5: Preparation of the Crystalline Form I of Belinostat

A mixture of the acetone solvate of Belinostat (65 g) and methanol (520 mL) was stirred for 20-30 minutes at 20-30° C. to obtain a clear solution. The resulting reaction mixture was added to water (1560 mL) and stirred for 2 hours at 20-30° C. The resulting mixture was filtered, washed with water (130 mL) and dried under vacuum. The resulting product was stirred in methanol (390 mL) for 20-30 minutes at 20-30° C. and filtered. The filtrate was added to water (1170 mL) and stirred for 2-3 hours at 20-30° C., filtered, washed with water and dried under vacuum to give 51 g of crystalline form I of Belinostat having purity 99.97% by HPLC.

We claim:

1. An acetone solvate of Belinostat, characterized by an X-ray powder diffraction (XRPD) pattern comprising peaks at about 16.3, 18.2, 21.0 and 22.3±0.2 degrees two-theta.

2. The acetone solvate of Belinostat according to claim 1, comprising about 8.5±1% by weight of acetone.

3. The acetone solvate of Belinostat according to claim 1, characterized by an X-ray powder diffraction (XRPD) pattern further comprising peaks at about 4.1, 8.2, 15.8 and 21.3±0.2 degrees two-theta.

4. The acetone solvate of Belinostat according to claim 1, characterized by an X-ray powder diffraction (XRPD) pattern substantially the same as depicted in FIG. 1.

5. A process for the preparation of the acetone solvate of Belinostat of claim 1, the process comprising the steps of:
   a. contacting Belinostat with acetone; and
   b. isolating the acetone solvate of Belinostat.

6. The process according to claim 5, wherein step a) is carried out at 10-70° C.

7. The process according to claim 5, wherein step a) is carried out for 10 minutes to 12 hours.

8. A pharmaceutical composition comprising the acetone solvate of Belinostat according to claim 1 and at least one pharmaceutically acceptable carrier.

9. The acetone solvate of Belinostat of claim 1, wherein the molar ratio of Belinostat to acetone solvent is about 1:0.75-0.95.

\* \* \* \* \*